US00PP26942P3

(12) United States Plant Patent
Lintott et al.

(10) Patent No.: US PP26,942 P3
(45) Date of Patent: Jul. 12, 2016

(54) ***GAILLARDIA* PLANT NAMED 'SUNSET SUNRISE'**

(50) Latin Name: *Gaillardia×grandiflora*
Varietal Denomination: Sunset Sunrise

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 87 days.

(21) Appl. No.: 14/544,055

(22) Filed: Nov. 19, 2014

(65) Prior Publication Data

US 2015/0150176 P1 May 28, 2015

Related U.S. Application Data

(60) Provisional application No. 61/963,168, filed on Nov. 25, 2013.

(51) Int. Cl.
*A01H 5/02* (2006.01)

(52) U.S. Cl.
USPC ..... Plt./431

(58) Field of Classification Search
USPC ..... Plt./431
See application file for complete search history.

*Primary Examiner* — Annette Para
(74) *Attorney, Agent, or Firm* — Bethany R. Roahrig; Barbara Campbell; Cochran Freund & Young, LLC

(57) ABSTRACT

A new cultivar of *Gaillardia* named 'Sunset Sunrise' that is distinguishable by a long blooming period, compact low-growing habit and large inflorescences which are vibrant yellow in color, with an orange-red inner ring and a central orange disc, is disclosed.

2 Drawing Sheets

Genus and species: *Gaillardia×grandiflora.*
Variety denomination: 'Sunset Sunrise'.

BACKGROUND

The present disclosure relates to a new and distinct cultivar of *Gaillardia* plant, also known as a blanket flower, a herbaceous perennial that is grown for use as an ornamental landscape and container plant. The new variety is known botanically as *Gaillardia×grandiflora* and will be referred to hereinafter by the cultivar name 'Sunset Sunrise'. *Gaillardia* is in the family Compositae, under which the commonly referred to "flower" is actually the inflorescence, and made up of smaller ray florets and disc florets. The ray florets themselves have the appearance of "petals".

'Sunset Sunrise' originated and was selected from a large population of hybrid seedlings from a *Gaillardia* breeding program which was started in 2006. The breeding program was conducted in a greenhouse nursery in West Sussex, United Kingdom. The aims of the breeding program were to produce novel combinations of flower colors and flower forms which are borne on well-branched plants with sturdy growth habits. A controlled hybridization was carried out using combinations of selected named varieties and selected unnamed and unreleased seedlings retained from previous breeding cycles.

'Sunset Sunrise' was selected in 2008 for its vibrant yellow inflorescences which exhibit an inner orange red ring (by virtue of the orange-red base to each ray floret) and a central orange disc. The ray florets are borne in two rows or layers and are produced from early spring until fall. 'Sunset Sunrise' was also selected for its compact growth habit.

The hybridization which led to the selection of 'Sunset Sunrise' was carried out during 2007 using the variety, *Gaillardia* 'Fanfare' (U.S. Plant Pat. No. 15,892) as the male parent and a proprietary unreleased and unnamed *Gaillardia* yellow seedling as the female parent.

'Sunset Sunrise' was first asexually propagated in September 2008 in a greenhouse at the inventors nursery in West Sussex, United Kingdom using shoot cuttings taken from lateral branches. 'Sunset Sunrise' is stable and reproduces true to type in successive generations of asexual reproduction.

SUMMARY

The following traits have been repeatedly observed and represent the distinguishing characteristics of 'Sunset Sunrise'. 'Sunset Sunrise' has not been tested under all possible conditions and phenotypic differences may be observed with variations in environmental, climatic, and cultural conditions, without however, any variance in genotype.

1. 'Sunset Sunrise' exhibits a compact and naturally branching plant habit;
2. 'Sunset Sunrise' exhibits single inflorescences composed of two rows or layers of ray florets;
3. The ray florets of 'Sunset Sunrise' are predominantly yellow in color, with an orange-red base which confers the appearance of an orange-red ring in the inflorescence;
4. The disc of 'Sunset Sunrise' is yellow when the inflorescence is newly opening, gradually becoming orange-red as the inflorescence and the disk florets age;
5. 'Sunset Sunrise' blooms continually from early spring until late fall;
6. After one year's growth in a 3 liter container, 'Sunset Sunrise' is 35 cm to 40 cm in height and 40 cm to 45 cm in width; and
7. 'Sunset Sunrise' is hardy in USDA zone 5.

DESCRIPTION OF THE PHOTOGRAPHS

The accompanying color photographs illustrate the overall appearance of the new *Gaillardia* cultivar 'Sunset Sunrise' showing the colors as true as it is reasonably possible to obtain in colored reproductions of this type. Colors in the photographs may differ from the color values cited in the detailed botanical description, which more accurately describes the actual colors of the new variety 'Sunset Sunrise'.

DESCRIPTION OF THE NEW VARIETY

Figure 1:
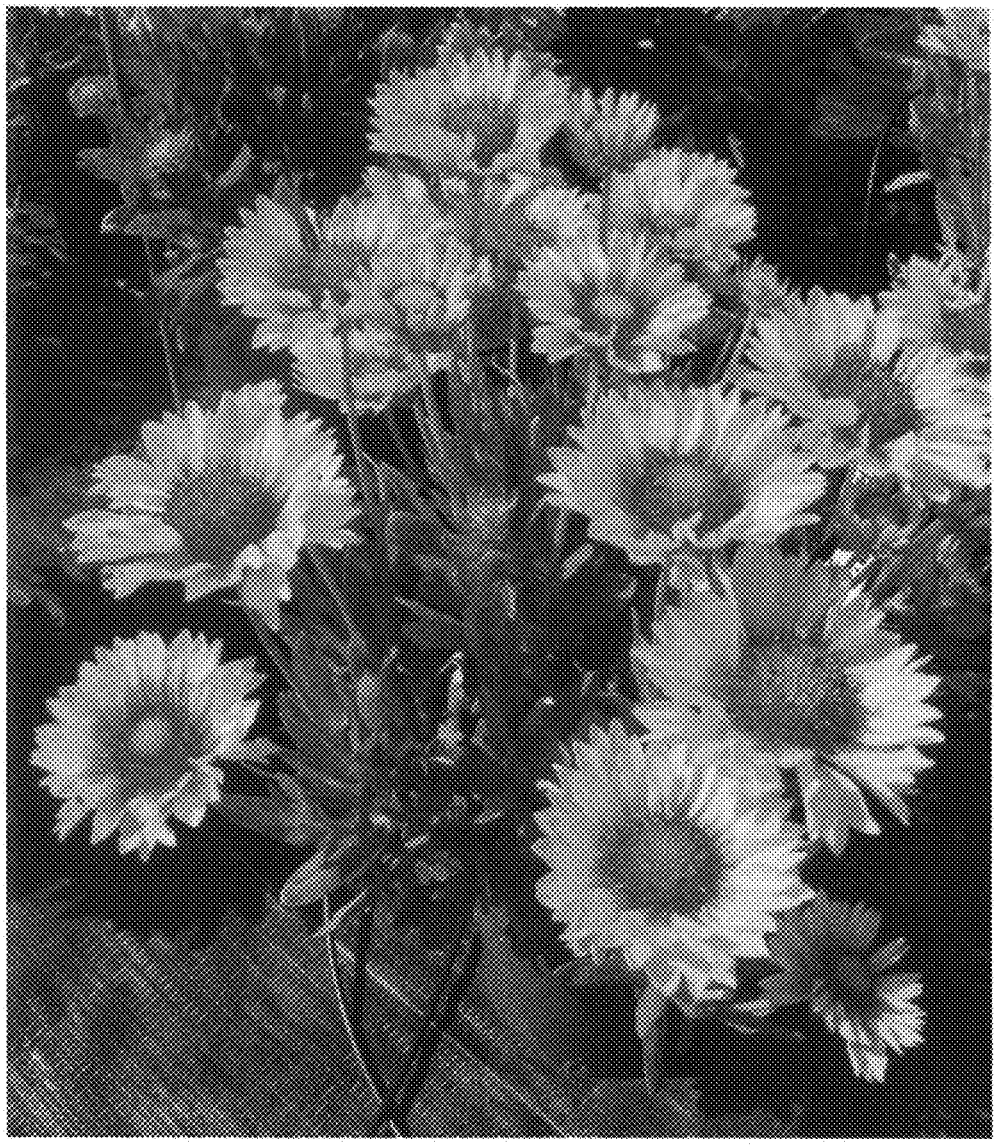
FIG. 1 depicts a whole plant of 'Sunset Sunrise' which has been grown in a frost-free greenhouse in West Sussex, United Kingdom. The illustrated plant is one year old and has been grown without any pinching or chemical growth regulator.
Figure 2:
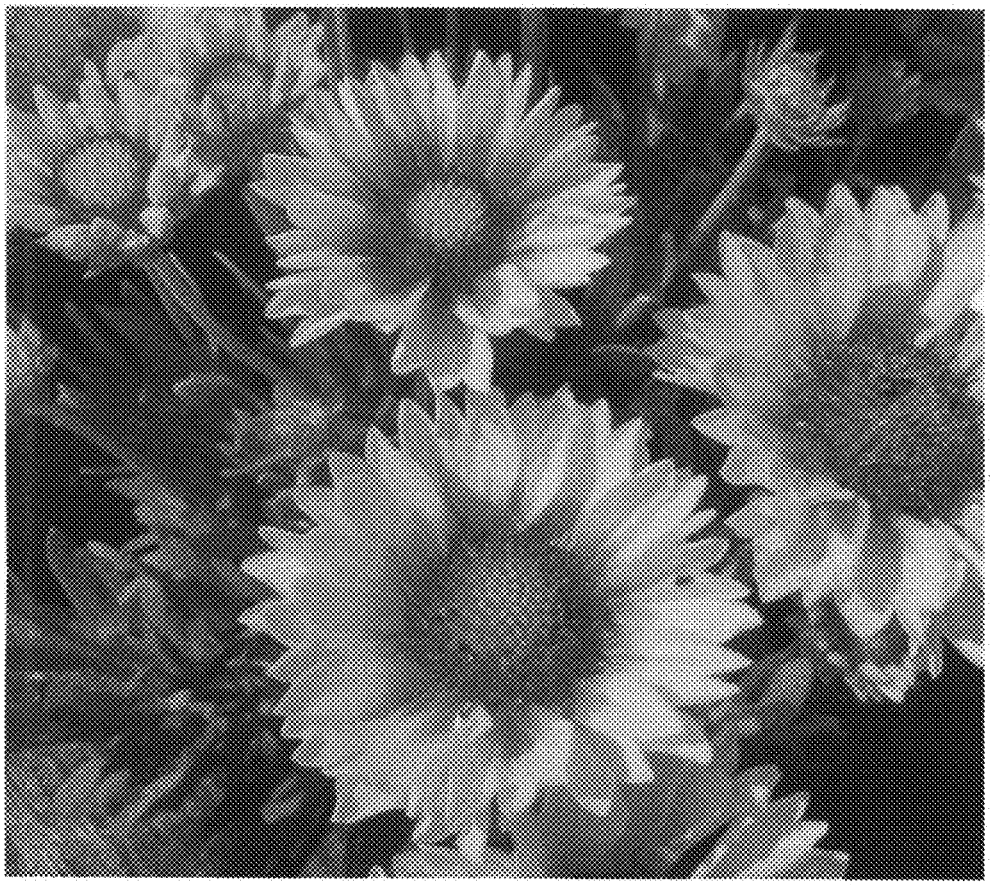
FIG. 2 depicts a close-up view of the fully expanded inflorescence of 'Sunset Sunrise'.

The following detailed descriptions set forth the distinctive characteristics of 'Sunset Sunrise'. Observations, measurements, values, and comparisons were collected in August, 2014 in Santa Barbara, Calif. from a one year old plant grown outdoors in full sun in freely drained proprietary peat-based potting soil. Color determinations were made in accordance with The 2007 Royal Horticultural Society Colour Chart from London England, except where general color terms of ordinary dictionary significance are used.

Classification:

*Family*.—Compositae.

*Genus*.—*Gaillardia*.

*Species*.—×*grandiflora*.

*Common name*.—Blanket flower.

Parentage:

*Female parent*.—Unnamed yellow seedling of *Gaillardia* (unpatented).

*Male parent*.—*Gaillardia* 'Fanfare' (U.S. Plant Pat. No. 15,892).

Plant:

*Propagation method*.—Typically by softwood cuttings although root cuttings have also been successful.

*Rooting system*.—Fine and fibrous.

*Vigor*.—Moderate vigor.

*Time to develop roots*.—14 to 20 days are needed for an initial cutting to develop roots.

*Temperature to develop roots*.—The recommended air temperature is 20-21° Centigrade.

*Crop time*.—Approximately 10 weeks to 2 months are needed to produce a 15-centimeter container from a rooted cutting.

*Growth habit*.—Compact and naturally freely branching.

*Suggested container size*.—15-centimeter container.

*Use*.—Ornamental for use as a landscape plant or container plant.

*Type*.—Herbaceous perennial.

*Overall dimensions*.—After one year's growth in a 3 liter container: 35 cm to 40 cm in height and 40 cm to 45 cm in width. At maturity in the ground: 40 cm to 45 cm in height and 50 cm to 55 cm in width.

*Cultural requirements*.—Grow in full sun with moderate water, and well-draining soil such as loam.

*Hardiness*.—USDA Zone 5.

*Growing requirements*.—If grown outside in regions which experience winter freezing, 'Sunset Sunrise' may be started as a cutting during the spring or summer of the previous year, planted out prior to the onset of winter, and flowering will commence typically in May or June according to the region and season. When grown outside in frost-free regions, or in frost-protected greenhouses, 'Sunset Sunrise' will flower virtually all year round and may be started as a cutting (which should be non-flowering) at any time of year.

Stems:

*Branching habit*.—Basal branching.

*Stem color*.—138B.

*Stem dimensions*.—10 cm to 15 cm in length and 5 mm in width.

*Stem shape*.—Cylindrical, slightly fluted longitudinally.

*Stem surface*.—Markedly villous with dense coverage of very fine silvery hairs, approximately 3 mm to 4 mm in length.

*Internode length*.—Average internode length is 10 mm to 12 mm.

Foliage:

*Type*.—Evergreen.

*Leaf arrangement*.—Alternate.

*Margin*.—Entire, except basal leaves slightly dentate with three rounded teeth, 1 mm to 3 mm in depth.

*Leaf shape*.—Oblanceolate.

*Leaf dimensions* (*base of plant*).—20 cm to 23 cm in length, 3.5 cm in width.

*Leaf dimensions* (*at inflorescence height*).—8 cm to 9 cm in length, 2 cm in width.

*Leaf base*.—Truncate.

*Leaf apex*.—Rounded.

*Leaf attachment*.—Sessile.

*Leaf color* (*both surfaces*).—138A.

*Leaf venation pattern*.—Parallel; mid vein protrudes on both surfaces.

*Vein color* (*both surfaces*).—138B.

*Leaf surface* (*both surfaces*).—Pubescent, very fine silvery hairs, lighter than 156D, approximately 3 mm in length.

*Fragrance*.—A slight sage-like scent when bruised.

Inflorescence:

*Inflorescence*.—Solitary.

*Aspect*.—Facing upward.

*Dimensions of inflorescence*.—80 mm in diameter and 15 mm in height.

*Inflorescence type*.—Radiate capitate with central disc.

*Disc diameter* (*inflorescence fully expanded*).—25 mm to 28 mm.

*Inflorescence number per plant*.—A one-year old plant bears approximately 30 to 35 inflorescences in bud and flower at one time.

*Blooming season*.—Spring, summer and fall.

*Lastingness of inflorescence*.—10 days, reducing to 7 days in full sun in mid-summer.

Peduncle:

*Peduncle dimensions*.—8 cm to 11 cm in length and 2.5 mm in diameter.

*Peduncle shape*.—Cylindrical.

*Peduncle surface*.—Surface is pubescent and exhibits longitudinal ridges.

*Peduncle color*.—138C.

*Peduncle strength*.—Stiff.

Flower buds:

*Bud shape*.—Rotate whorl.

*Bud dimensions* (*bud*).—13 mm in diameter and 8 mm in height.

*Bud color*.—138B.

*Bud surface*.—Villous.

Ray florets:

*Ray floret shape*.—Fan-shaped, predominantly with 3 fused petals appearing as lobes. One or two ray florets in each inflorescence comprised of 2 fused petals.

*Ray floret surface* (*abaxial surface*).—Pubescent.

*Ray floret surface* (*adaxial surface*).—Glabrous.

*Ray floret color* (*abaxial surface*).—13B throughout.

*Ray floret color* (*adaxial surface*).—43B extending 20 mm from base; 17B extending 12 mm from apex.

*Ray floret arrangement*.—Radiate.

*Number of ray florets per inflorescence*.—15 to 18 ray florets per inflorescence.

*Number of petals per ray floret*.—Three.

*Fused or unfused*.—Petals are basally fused.

*Petal margins of ray floret*.—Entire.

*Ray floret dimensions*.—32 mm in length including the corolla tube, 16 mm in width at the widest point.

*Corolla tube dimensions*.—5 mm in depth and 1.0 mm in diameter.

*Ray floret veins* (*both surfaces*).—Longitudinal, parallel, fine but prominent; color N34A.

*Self-cleaning or persistent*.—Self-cleaning.

Disc florets:

*Quantity of disc florets per inflorescence*.—Numerous, approximately 200 to 250.

*Disc floret dimensions* (*including pistil length*).—9 mm in length and 2.5 mm in width.

*Depth of disc floret corolla tube*.—6 mm.

*Surface of disc florets*.—Lanate.

*Color of disc florets* (*inflorescence newly opening, both surfaces*).—12A.

*Color of disc florets* (*inflorescence fully expanded, both surfaces*).—N34A.

*Phyllary*.—Dimensions: 5.50 cm in diameter and 3 cm in length. Color: 147B. Arrangement: Whorl.

*Involucral bracts*.—Number: An average of 25 per inflorescence. Shape: Oblanceolate. Dimensions: 1.0 cm to 1.5 cm in length and 0.4 cm to 0.8 cm in width. Margin: Entire. Apex: Acute. Base: Truncate. Color (both surfaces): 138B. Surface texture (both surfaces): Pubescent.

*Fragrance of inflorescence*.—Sweet fragrance.

Reproductive organs:

*Stamens* (*present on disc florets only*).—Number: Three, adnate to inner surface of corolla tube. Dimensions: Bifid, 10 mm to 12 mm in length, exserted 8 mm to 9 mm; 0.2 mm in width. Color: 187B. Form: Plumose. Anther: Dimensions: 0.50 mm in length and 1 mm in width. Color: 187A. Shape: Narrow lanceolate. Pollen: Present. Quantity: Large amount. Color: 17C.

*Pistil* (*present on ray florets and disc florets*).—Number: One per floret. Pistil length: 12 mm in length. Style dimensions: 2 mm in length and 1 mm in width. Style color: 150D. Stigma: Dimensions: 8 mm in length and 1.75 mm in width. Form: Plumose. Color: 187A. Shape: Bifurcate. Ovary: Position: Inferior. Color: 150D. Shape: Globose. Dimensions: 1 mm in width and 2 mm in height.

Fruit/seed set:

*Number of seeds*.—Small to moderate amount (ranges from 50 to 100 seeds per inflorescence).

*Seed dimensions*.—5 mm to 6 mm in length (including hairs at apex) and 1 mm to 2 mm in diameter.

*Seed color*.—200A.

*Seed shape*.—Conical with rounded base and apex.

*Seed surface*.—Smooth except at the apex where many very fine silver hairs, up to 2 mm in length, are present in circular groups.

Disease and pest susceptibility: 'Sunset Sunrise' has not been observed to exhibit any resistance to any particular pest or disease. 'Sunset Sunrise' is susceptible to downy mildew and to thrips as may be typical of *Gaillardia*.

COMPARISON WITH PARENTAL LINES AND KNOWN VARIETY

'Sunset Sunrise' is distinguishable from the female parent, unnamed and unreleased *Gaillardia* yellow seedling as follows: The flowers of 'Sunset Sunrise' are vibrant orange-yellow in color, whereas the flowers of the female parent are entirely yellow in color. 'Sunset Sunrise' exhibits a more compact growth habit and lighter gray-green foliage than the female parent.

'Sunset Sunrise' is distinguishable from the male parent, *Gaillardia* 'Fanfare' (U.S. Plant Pat. No. 15,892) as follows: Whereas the male parent bears flowers with tubular ray florets, the flowers of 'Sunset Sunrise' consist of two rows of flat ray florets. Additionally 'Sunset Sunrise' is more floriferous than the male parent and the growth habit is less vigorous.

The variety of *Gaillardia* which is considered to most closely resemble 'Sunset Sunrise' is 'Oranges and Lemons' (U.S. Plant Pat. No. 17,092). The flowers of 'Oranges and Lemons' are smaller in size than 'Sunset Sunrise'. Additionally, the flowers of 'Sunset Sunrise' are longer lasting than those of 'Oranges and Lemons'.

We claim:

1. A new and distinct cultivar of *Gaillardia* plant named 'Sunset Sunrise' as described and illustrated herein.

* * * * *